United States Patent [19]

Shanbrom

[11] 4,315,919

[45] Feb. 16, 1982

[54] DEPYROGENATION PROCESS

[76] Inventor: Edward Shanbrom, 2252 Liane La., Santa Ana, Calif. 92705

[21] Appl. No.: 194,263

[22] Filed: Oct. 6, 1980

[51] Int. Cl.³ ...................... A61K 35/14; A61K 37/00
[52] U.S. Cl. .................................... 424/177; 424/101
[58] Field of Search ................. 424/78, 101, 199, 177, 424/243, 303, 311, 315, 316, 319, 325, 329, 335, 339, 340

[56] References Cited

PUBLICATIONS

Mochida et al.–Chem. Abst. vol. 76, (1972) p. 21481s.
E. Work, "Production, Chemistry and Properties of Bacterial Pyrogens and Endotoxins" in Pyrogens and Fever, Ciba Foundation Symposium, 1971, pp. 23–47, Churchill Livingstone.
Chemical Abstracts, vol. 85, 190481h, 1976.

*Primary Examiner*—Sam Rosen
*Attorney, Agent, or Firm*—Eric P. Schellin

[57] ABSTRACT

Biological and pharmaceutical products which are contaminated with pyrogens are depyrogenated by prolonged contact with a solution or suspension of from about 0.25% to about 10% by weight of a non-denaturing amphiphile.

10 Claims, No Drawings

DEPYROGENATION PROCESS

BACKGROUND OF THE INVENTION

This invention relates to a method of depyrogenating biological and pharmaceutical products.

In the development and production of biological and pharmaceutical products and particularly various proteinaceous substances used for biomedical and therapeutic purposes, the problem of contamination with pyrogens (endotoxins) is ever present.

Pyrogens are lipopolysaccharides (LPS) derived from the outer cell wall of gram-negative bacteria. They are toxic materials which are also known as "endotoxins" to distinguish them from toxic substances synthesized and excreted by the intact bacterium. Pyrogens have numerous biologic activities which include the production of fever, activation of clotting mechanisms and induction of shock. Consequently, it is essential that pyrogenic substances be removed and the causative bacteria be rendered innocous by sterilization or other such treatment of the final biological or pharmaceutical product.

Prior methods for inactivation of pyrogens comprise extensive and rigorous treatment with heat, acid or alkali, filtration of insoluble pyrogens or removal by adsorption with gels, ion-exchange resins and various other such adsorbent materials. Most of these methods are burdensome, time-consuming and costly.

Further background on the properties and effects of pyrogens can be had by reference to a paper by Elizabeth Work entitled "Production, Chemistry and Properties of Bacterial Pyrogens and Endotoxins" in "Pyrogens and Fever", Ciba Foundation Symposium, 1971, pp. 23–47, edited by Wolstenholme and Birch, published by Churchill Livingstone; and a paper by D. C. Morrison and R. J. Ulevitch entitled "The Effects of Bacterial Endotoxins on Host Mediation Systems" in *Amer. J. Pathol.* 93(2), 527–601 (1978).

DESCRIPTION OF THE INVENTION

In accordance with the present invention, biological and pharmaceutical products are depyrogenated by prolonged contact with a solution or suspension of from about 0.25% to about 10% by weight of a non-denaturing amphiphile.

As used herein, the term "amphipile" is meant to define a substance containing both hydrophilic water-soluble and hydrophobic water-insoluble groups. Amphiphiles are generally classified into various groups and frequently into the anionic, cationic, ampholytic and nonionic surfactants. The following are well-known examples of commercially available amphiphiles:

Anionic

Sulphated oxyethylated alkylphenol (Triton W-30);
Sulphated lauryl ether alcohol;
Sodium dodecylbenzenesulfonate (Nacconol NR);
Sodium 2-sulfoethyl oleate (Igepon A);
Sodium N-methyl-N-oleylethanol sulfonate (Igepon T);
Sodium dodecylsulfate;
Sodium cholate;
Sodium deoxycholate;
Sodium dodecylsulfonate;
Sodium dodecyl-N-sarcosinate.

Cationic

Dodecyldimethylbenzylammonium chloride (Triton K-60);
Oxyethylated amines (Ethomeen);
Cetyltrimethylammonium bromide;
Tetradecylammonium bromide;
Dodecylpyrimidinium chloride;
Hexadecyltrimethylammonium chloride.

Ampholytic

Dodecyl $\beta$-alanine;
N-dodecylaminoethanesulfonic acid;
Palmitoyllysolecithin;
Dodecyl-N-betaine.

Nonionic

Ethylene oxide-propylene oxide condensates (Pluronic block copolymers) such as described in U.S. Pat. No. 2,674,619;
Oxyethylated alkylphenol (Triton X-100);
Partial esters of $C_{12-22}$ fatty acids (e.g. lauric, palmitic, stearic and oleic acids) and hexitol anhydrides (e.g. hexitans and hexides) (Spans) such as described in U.S. Pat. Nos. 2,232,820; 2,232,821; 2,303,432;
Polyoxyethylated derivatives of said partial esters made by adding poloxyethylene chains to the nonesterified hydroxyls (Tweens, e.g. Tween 80 or Polysorbate 80) such as described in U.S. Pat. No. 2,380,166;
Poloxyethylene partial fatty acid esters (Myrj 45);
Poloxyethylene fatty alcohol ethers (Brij).

The nonionic surfactants are preferred amphiphiles for use in this invention. The most preferred amphiphiles are the nonionic surfactants having a high water solubility and selected from the group consisting of substances having the general formula $RC_6H_4(OC_2H_4)_nOH$ wherein R is octyl or nonyl and n is at least 3. A most preferred substance of the foregoing general formula is octyl phenoxy polyethoxy ethanol. Surfactants of the latter type are available commercially from Rohm & Haas Co. under the trademark "Triton X", e.g., Triton X-100, Triton X-165, Triton X-205, Triton X-305 and Triton X-405. Another such nonionic surfactant is nonyl phenoxy polyethoxy ethanol which is available commercially under the trademark "Triton N-100".

Another preferred group of amphiphiles are the salts of bile acids such as sodium cholate and sodium deoxycholate.

Treatment of the biological and pharmaceutical products with the amphiphile can be carried out at any stage in the production sequence. Preferably, the depyrogenation treatment is carried out following the last step at which contamination with pyrogens is likely to occur. In those instances where pyrogen contamination occurs at a production stage following a previous depyrogenation, it may be necessary to subject the product to a further depyrogenation treatment in accordance with the method of this invention. The method of the invention also is useful for reworking biological and pharmaceutical products that have become pyrogenic in a normal production run.

The period of time during which the biological and pharmaceutical products are contacted with the amphiphile should be sufficient to depyrogenate the product. Generally, a period of from about 30 minutes to about four hours at a temperature of from about 4° C. to about 37° C. is adequate to provide the desired depyrogenation.

Testing for the presence of pyrogens and to ensure adequate depyrogenation can be carried out by the standard qualitative fever response test in rabbits for pyrogens or by more recently developed Limulus lysate (amebocytes) assay procedures for pyrogens (LAL tests). The latter tests are based on gelling of a pyrogenic preparation in the presence of the lysate of the amebocytes of the horseshoe crab (Limulus polyphemus). See, e.g., U.S. Pat. No. 4,096,091 for a typical LAL test.

The contact of the biological and pharmaceutical products with the amphiphile can be carried out by washing the product with a solution or suspension of the amphiphile, or by immersing or soaking the product in such solution or suspension or by admixing with such solution or suspension.

The present invention is applicable to any biological or pharmaceutical product which because of its intended use in humans or administration to humans for biomedical or therapeutic purposes should be free of pyrogens and otherwise sterile. It is particularly adapted for depyrogenating those products which can not be adequately depyrogenated by heat or pH adjustments. Many proteinaceous products fall in the latter category due to the potential denaturation or destruction of the active material which can be caused by the prolonged rigorous treatment with heat, acid or alkali. For treatment of such proteinaceous products the amphiphile should be non-protein-denaturing.

Examples of biological and pharmaceutical products which can be depyrogenated in accordance with the present invention are:

Blood and blood fractions such as antihemophilic factor A (AHF, Factor VIII); prothrombin complex (Factors II, VII, IX AND X); gamma globulin; albumin;

Parenteral products such as intravenous solutions;

Biomedical implants such as heart valves;

Biological and pharmaceutical products derived from animal origin, e.g., insulin and other hormones, enzymes;

Biological products involved in or derived from tissue culture techniques;

Vaccines, including substances derived from animal and microbial sources;

Biological products derived from human or animal placenta;

Pharmaceutical and drug products in which the crude drug product is produced by fermentation of microorganisms which generate endotoxins;

Pharmaceutical and drug products which are processed in equipment having a residue of microbial contamination;

Products prepared by recombinant DNA or gene-splicing techniques and in which the product is elaborated by genetically engineered microorganisms such as in E. coli, e.g., strain K12, or Bacillus subtilis and the like. Examples of such products and the applicable technology can be had be reference to British UK Patent Application No. 2,018,778; European Patent Applications 6694 and 9930; Belgian Pat. No. 867,424; U.S. Pat. No. 4,190,495; and German Offenlegungsshriften Nos. 2,848,051; 2,848,052; 2,848,053; 2,923,927; and 2,940,525.

In the case of certain biological and pharmaceutical products, especially plasma protein products, it will be desirable to remove the amphipile following the prolonged contact with the plasma protein product. Removal of the amphiphile can be carried out by various precipitation steps in which the plasma proteins are precipitated while the amphiphile remains dissolved or suspended in the supernatant. Conventional plasma protein precipitants can be used for this purpose such as, e.g., polyethylene glycol, Pluronic polymers, glycine, ammonium sulfate, alcohol and rivanol.

Although certain amphiphiles such as sodium deoxycholate have been reported heretofore as able to dissociate or disaggregate endotoxins, the disaggregation has been described as reversible in the presence of the amphiphile tested. These amphiphiles thus have not been previously suggested as able to produce irreversible disaggregation of endotoxins such as to make them practical for the treatment of plasma protein products which are to be used for human administration. See, e.g., the paper by Elizabeth Work, cited hereinbefore. In accordance with the present invention biological protein products can be precipitated with protein precipitants after treatment with the amphiphile to destroy the endotoxins followed by separation and removal of the amphiphile in the supernatant. In such case it has been found that the Lipid A or most active portion of the endotoxin which normally is insoluble in water, remains with the amphiphile in the supernatant. The disaggregation is irreversible and treatment previously believed unuseful is now rendered practical.

The following examples will further illustrate the invention although it will be understood that the invention is not limited to these specific examples.

EXAMPLE 1

Whole human blood plasma was diluted 1:2 with pyrogen-free water and then spiked with ten micrograms of E. coli endotoxin. Triton X-100 was added to a concentration of 2% and the mixture was then incubated at 37° C. for one hour. Three dilutions of the treated mixture were then made and the dilutions were tested for pyrogenicity by the Limulus lysate (amebocytes) assay (LAL test) with the following results:

| Blood Dilutions | Endotoxin Amount | % Triton X-100 | LAL Reaction |
|---|---|---|---|
| 1:10 | 1 microgram | 0.2 | Negative |
| 1:100 | 0.1 microgram | 0.02 | " |
| 1:1000 | 0.01 microgram | 0.002 | " |

EXAMPLE 2

A commercially produced vial (lyophilized) of prothrombin complex (25 units of Factor IX per ml when reconstituted) was reconstituted with ten ml of sterile water. Triton X-100 was added to a concentration of 2% and the mixture was incubated ninety minutes at ambient temperature (ca. 20°-22° C.). To nine ml of the above mixture was added 6.0 ml of a 50% solution of polyethylene glycol 4000. The pH was adjusted to 5.7 and the mixture was cooled to below 5° C. to precipitate the protein. The mixture was centrifuged and the precipitate was resuspended in sterile water. The treated product was tested for pyrogenicity by the LAL test and compared with the original untreated sample and a control which consisted of the aforesaid precipitate of the treated sample to which 40 picograms of endotoxin were added. The following results were observed:

|  | LAL Reaction | | | |
| --- | --- | --- | --- | --- |
| Dilutions | 1:10 | 1:20 | 1:40 | 1:80 |
| Original Sample Untreated | pos. × 2 | pos. × 2 | pos. × 2 | pos. × 2 |
| Precipitate of Sample with 40 picograms Endotoxin | neg.* | pos. × 2 | pos. × 2 | pos. × 2 |
| Triton X-100 treated Precipitate | neg. × 2 | neg. × 2 | neg. × 2 | neg. × 2 |

*Due to heparin inhibitory effect at this dilution
pos. × 2 = positive in duplicate testing
neg. × 2 = negative in duplicate testing

EXAMPLE 3

Similar depyrogenation of endotoxin-contaminated albumin is obtained by treatment with 2% Triton X-100 as in Examples 1 and 2, above, or with 2% Polysorbate 80.

EXAMPLE 4

Similar depyrogenation of endotoxin-contaminated fibrinogen is obtained by treatment with 2% Triton X-100 as in Examples 1 and 2, above, or with 2% Polysorbate 80.

EXAMPLE 5

Human growth hormone derived by recombinant DNA techniques from *E. coli* strain K12, was treated with 3% Triton X-100 for two hours and reprecipitated with ammonium sulfate. The pyrogen level in the product was reduced from 2.2 nanograms/ml in the untreated product to less than 10 picograms/ml in the treated product.

Various other examples will be apparent to the person skilled in the art after reading the present disclosure without departing from the spirit and scope of the invention and it is intended that all such examples be included within the scope of the appended claims.

What is claimed is:

1. The method of depyrogenating a proteinaceous biological or pharmaceutical product comprising
    (1) treating said proteinaceous biological or pharmaceutical product by prolonged contact with a solution or suspension of from about 0.25% to about 10% by weight of a non-denaturing amphiphile,
    (2) adding to the resulting treatment mixture a protein precipitant for said proteinaceous biological or pharmaceutical product to thereby cause precipitation of said proteinaceous product and
    (3) separating from the resulting precipitate the supernatant which contains said amphiphile together with endotoxin dissociated or disaggregated by said prolonged contact.

2. The method of claim 1 in which the amphiphile is a bile acid salt selected from the group consisting of sodium cholate and sodium deoxycholate.

3. The method of claim 1 in which the amphiphile is a nonionic surfactant.

4. The method of claim 3 in which the nonionic surfactant is selected from the group consisting of the polyoxyethylated derivatives of partial esters of $C_{12-22}$ fatty acids and hexitol anhydrides.

5. The method of claim 4 in which the nonionic surfactant is Polysorbate 80.

6. The method of claim 3 in which the nonionic surfactant is selected from the group consisting of substances having the general formula $RC_6H_4(OC_2H_4)_nOH$ wherein R is octyl or nonyl and n is at least 3.

7. The method of claim 6 in which the nonionic surfactant is octyl phenoxy polyethoxy ethanol.

8. The method of claim 7 in which the concentration of the surfactant is about 2–3%.

9. The method of claim 1 in which the treated product is derived from fermentation processes.

10. The method of claim 9 in which the amphiphile is octyl phenoxy polyethoxy ethanol.

* * * * *